(12) United States Patent
Farrow et al.

(10) Patent No.: US 11,344,452 B2
(45) Date of Patent: May 31, 2022

(54) COMPRESSION GAUGE FOR THERAPEUTIC COMPRESSION GARMENTS

(71) Applicant: Farrow Innovations LLC, Bryan, TX (US)

(72) Inventors: Wade P. Farrow, College Station, TX (US); Barry L. Creighton, College Station, TX (US)

(73) Assignee: FARROW INNOVATIONS LLC, Bryan, TX (US)

( * ) Notice: Subject to any disclaimer, the term of this patent is extended or adjusted under 35 U.S.C. 154(b) by 196 days.

(21) Appl. No.: 16/839,820

(22) Filed: Apr. 3, 2020

(65) Prior Publication Data

US 2020/0268557 A1 Aug. 27, 2020

Related U.S. Application Data

(63) Continuation of application No. 14/732,467, filed on Jun. 5, 2015, now abandoned.

(60) Provisional application No. 62/008,118, filed on Jun. 5, 2014.

(51) Int. Cl.
| | |
|---|---|
| *A61F 13/00* | (2006.01) |
| *A61F 13/08* | (2006.01) |
| *A61H 9/00* | (2006.01) |
| *A61F 13/10* | (2006.01) |

(52) U.S. Cl.
CPC .. *A61F 13/00038* (2013.01); *A61F 13/00059* (2013.01); *A61F 13/08* (2013.01); *A61H 9/0078* (2013.01); *A61F 13/10* (2013.01); *A61F 2013/00123* (2013.01); *A61H 2201/165* (2013.01)

(58) Field of Classification Search
CPC ......... A61F 13/00038; A61F 13/00059; A61H 9/0078; A61H 2201/165
USPC ....................................................... 601/150
See application file for complete search history.

(56) References Cited

U.S. PATENT DOCUMENTS

| | | |
|---|---|---|
| 5,036,838 A | 8/1991 | Sherman |
| 5,195,950 A | 3/1993 | Delannoy |
| 5,387,183 A | 2/1995 | Jones |
| 5,779,659 A | 7/1998 | Allen |

(Continued)

FOREIGN PATENT DOCUMENTS

| | | |
|---|---|---|
| WO | 1999036019 A1 | 7/1999 |
| WO | 2000015139 A2 | 3/2000 |

OTHER PUBLICATIONS

3M Coban 2 Layer Compression System, Commonly Asked Questions, Feb. 13, 2007, pp. 1-3.

(Continued)

*Primary Examiner* — Andrew S Lo
(74) *Attorney, Agent, or Firm* — Shumaker, Loop & Kendrick, LLP

(57) ABSTRACT

A method and apparatus for treating edema is disclosed. The method may include obtaining a compression garment comprising material having an end stretch. At least one gauge may be applied to the material. The compression garment may be applied to a patient. During the applying, the material may be stretched until the at least one gauge indicates that a proper amount of stretch has been reached. The at least one gauge may be tuned so that the material arrives at or near end stretch at substantially the same time that the at least one gauge indicates that the proper amount of stretch has been reached.

21 Claims, 6 Drawing Sheets

(56) References Cited

U.S. PATENT DOCUMENTS

| | | | |
|---|---|---|---|
| 6,152,893 | A | 11/2000 | Pigg et al. |
| 6,338,723 | B1 | 1/2002 | Carpenter et al. |
| 6,360,615 | B1 | 3/2002 | Smela |
| 6,432,074 | B1 | 8/2002 | Ager |
| 7,329,232 | B2 | 2/2008 | Lipshaw et al. |
| 7,942,838 | B2 | 5/2011 | Farrow |
| 8,491,514 | B2 | 7/2013 | Creighton et al. |
| 2005/0209545 | A1 | 9/2005 | Farrow et al. |
| 2007/0179421 | A1 | 8/2007 | Farrrow |
| 2010/0056973 | A1 | 3/2010 | Farrow et al. |
| 2010/0312160 | A1 | 12/2010 | Creighton et al. |
| 2012/0010551 | A1 | 1/2012 | Farrow et al. |
| 2012/0238923 | A1 | 9/2012 | Yamashita et al. |
| 2013/0137943 | A1* | 5/2013 | Pinto Rodrigues .. A61B 5/4872 600/301 |
| 2013/0296763 | A1 | 11/2013 | Farrow et al. |
| 2013/0319128 | A1 | 12/2013 | Richardson et al. |
| 2014/0276274 | A1 | 9/2014 | Clare et al. |
| 2014/0276275 | A1 | 9/2014 | Stokes et al. |
| 2014/0296749 | A1* | 10/2014 | Reid, Jr. .................. D04B 1/12 600/587 |
| 2016/0030251 | A1 | 2/2016 | Schuren et al. |
| 2016/0220185 | A1 | 8/2016 | Richardson et al. |
| 2016/0220808 | A1* | 8/2016 | Hyde ................... A61B 5/6895 |
| 2017/0172835 | A1 | 6/2017 | Richardson et al. |
| 2020/0316365 | A1* | 10/2020 | Hyde ....................... A61H 1/00 |
| 2021/0153748 | A1* | 5/2021 | Rapp ........................ A61B 5/01 |

OTHER PUBLICATIONS

3M Coban 2 Layer Compression System, Patient Instructions, 2006, 1 page.

New 3M Coban 2 Layer Compression System Introduced for the Treatment of Edema Associated with Venous Leg Ulcers, Press Release, May 1, 2006, pp. 1-3.

Hawkins, A New Cohesive Short-Stretch Bandage and Its Application, British Journal of Nursing, Feb. 22, 2001-Mar. 7, 2001, pp. 249-253.

Understanding Compression Therapy, Medical Education Partership, Ltd, 2003, pp. 1-17.

* cited by examiner

COMPRESSION GAUGE FOR THERAPEUTIC COMPRESSION GARMENTS

RELATED APPLICATIONS

This application claims the benefit of U.S. Non-Provisional application Ser. No. 14/732,467 filed Jun. 5, 2015 which claims the benefit of U.S. Provisional Patent Application Ser. No. 62/008,118 filed Jun. 5, 2014, which is hereby incorporated by reference.

BACKGROUND

Field of the Invention

This disclosure relates to apparatus, methods, and systems for treating medical conditions by application of controlled compression to general and specific areas of a human or animal body.

BACKGROUND OF THE INVENTION

Excessive interstitial fluid accumulation, referred to as edema, may arise from a variety of illnesses and conditions, including trauma, post-surgical recovery, a medicated conduction, congestive heart failure, renal insufficiency, venous valvular insufficiency, postphlebotic syndrome, and lymphedema. Compression methods and systems control edema by reducing interstitial fluid. This in turn may increase nutrient delivery to tissues, remove waste from tissues, relieve pain from swelling, increase tissue oxygenation, promote wound healing, and decrease risk of infection. However, typical compression technologies have certain drawbacks.

For example, in applying or donning a compression garment, it can be difficult for a patient, caregiver, or medical professional to accurately predict the compression that will be produced. Accordingly, it may be difficult to accurately and repeatably apply to the patient the prescribed level of therapeutic compression. What is needed is an improved compression garment that enables patients, caregivers, and/or medical professionals an easy way to determine that the prescribed level of therapeutic compression is being applied to the patient.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

Figure 1:
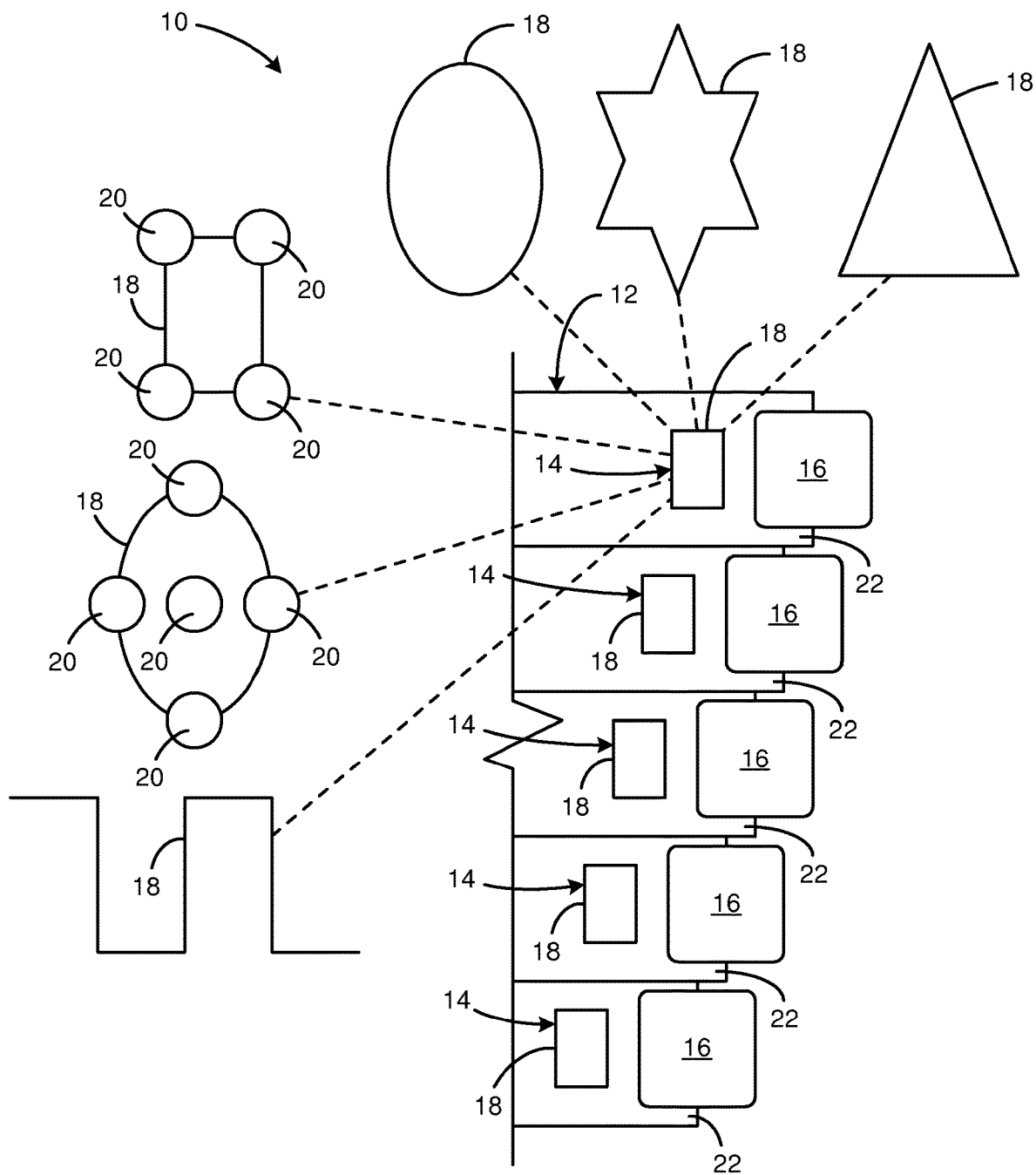
FIG. 1 is a schematic diagram illustrating a portion of one embodiment of a therapeutic system in accordance with the present invention with the compression gauges thereof in an unstretched or neutral position.
Figure 2:
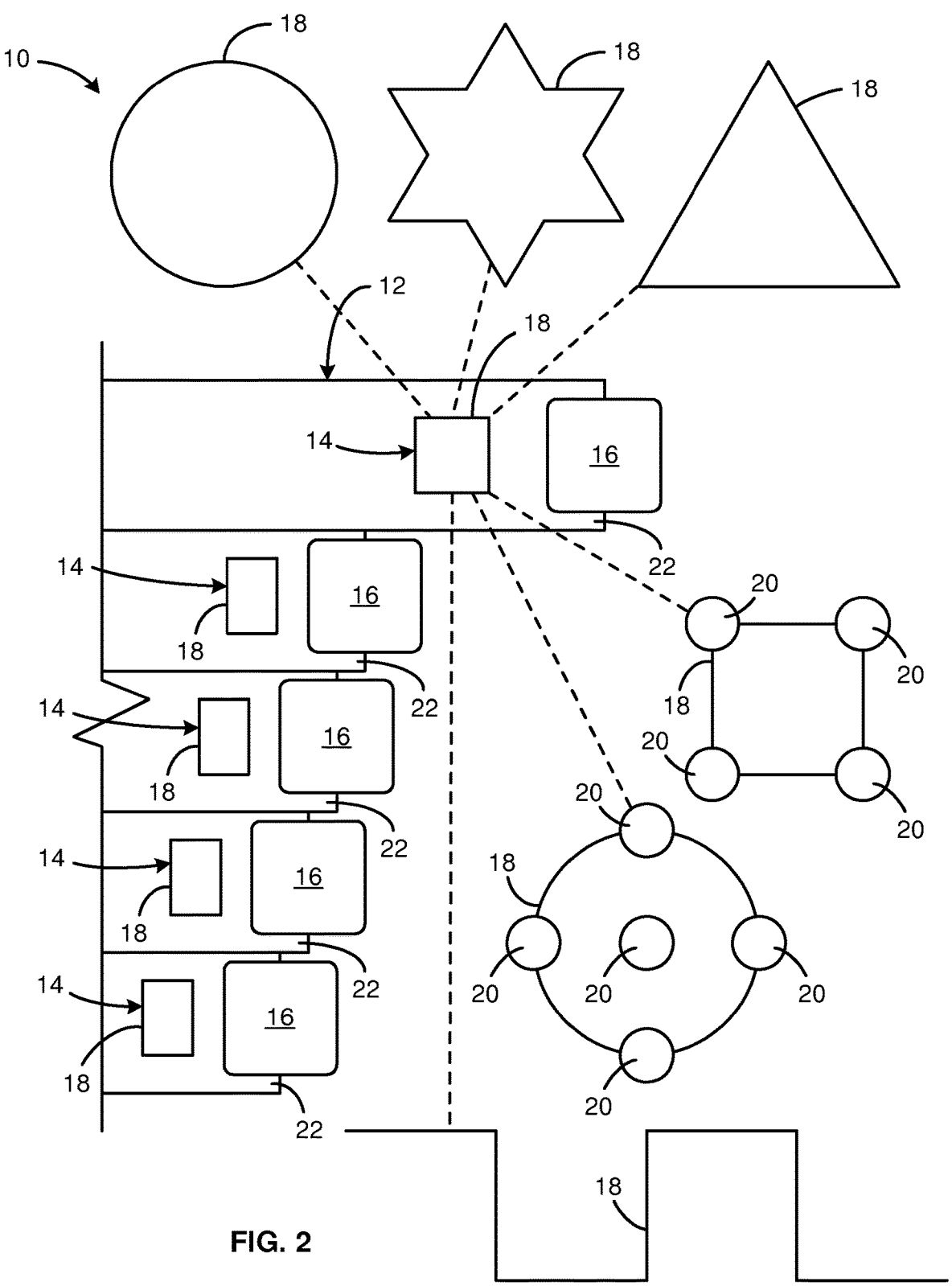
FIG. 2 is a schematic diagram of the therapeutic system of FIG. 1 with a portion of the compression garment and a corresponding gauge being stretched an appropriate amount.
Figure 3:
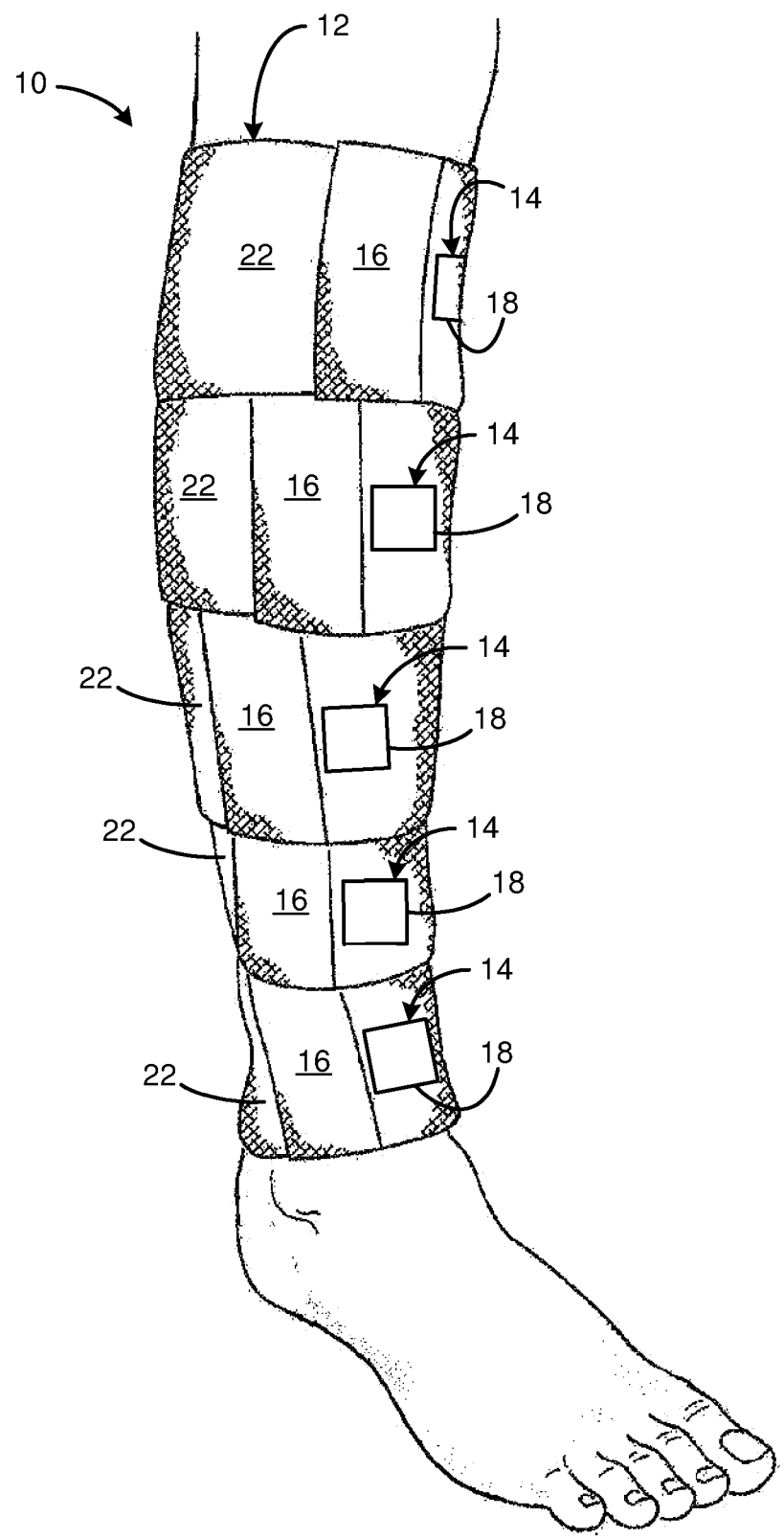
FIG. 3 is an illustration of one embodiment of a band-based therapeutic system with the compression gauges thereof stretched an appropriate amount.
Figure 4:
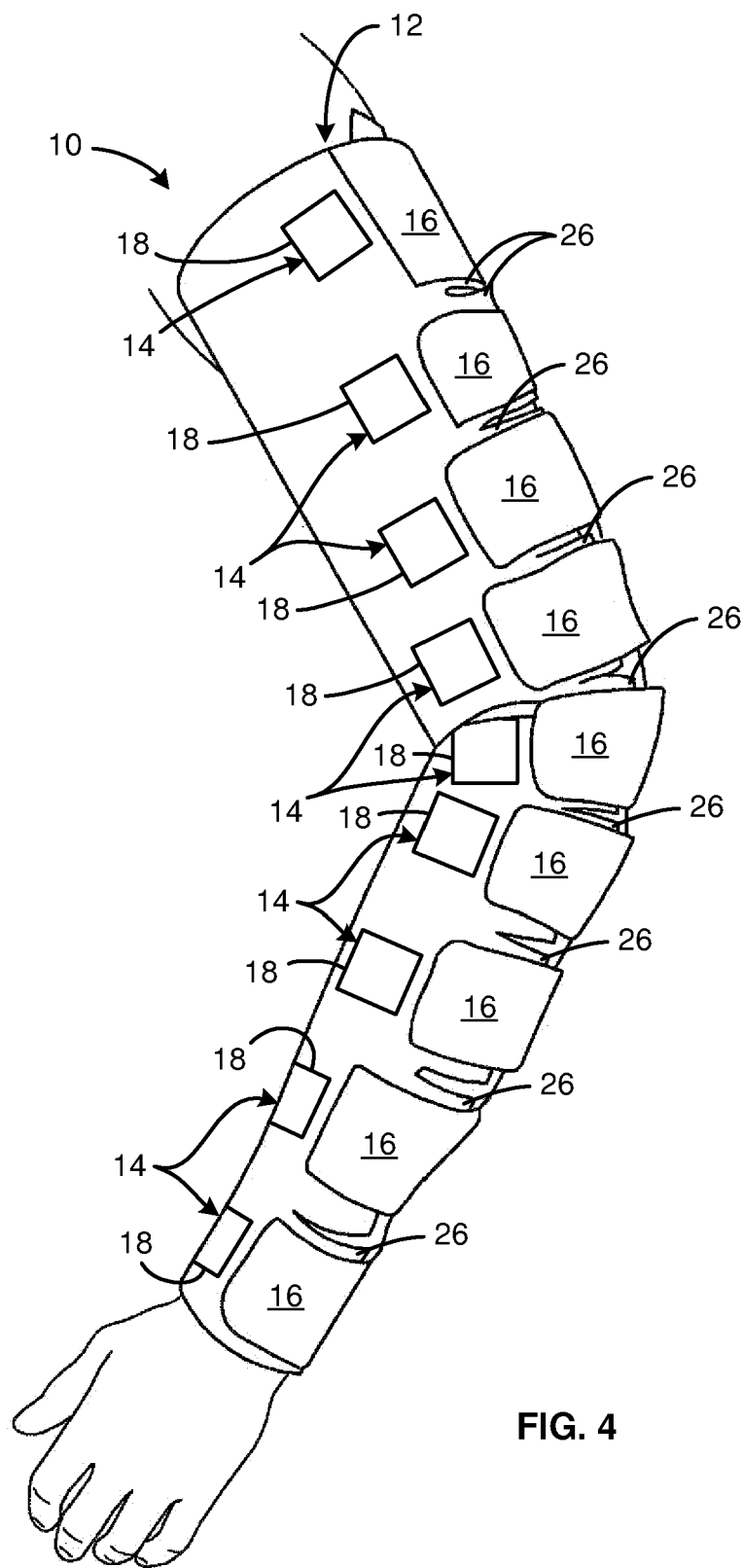
FIG. 4 is an illustration of one embodiment of a therapeutic system comprising a sheet with tabs and compression gauges that are stretched an appropriate amount.
Figure 5:
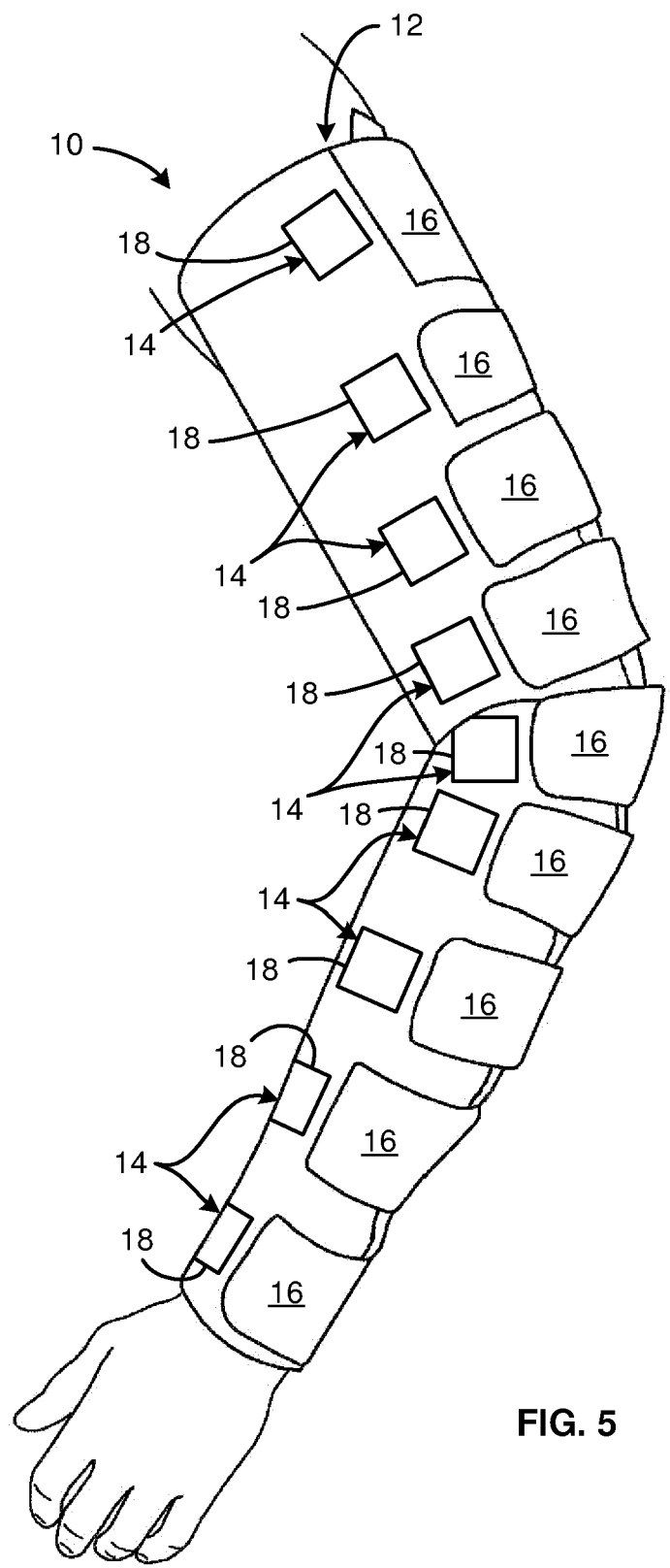
FIG. 5 is an illustration of one embodiment of a therapeutic system comprising a substantially continuous sheet and compression gauges that are stretched an appropriate amount.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Compression garments applied at or near end-stretch may prevent edema reaccumulation while maximizing a muscle-pump function (e.g., calf muscle venous return). For example, compression garments may be applied at or near end-stretch, which may provide a baseline or resting compression when the patient is supine. The compression level may increase if the patient is sitting or standing. Such an increase in compression may be relative to the vertical distance between the patient's heart and the location on their limb.

When a patient activates their musculature, such as in calf muscle augmentation, it may increase venous blood return to the heart and improve lymphatic flow by muscle activated venous pumping action. Thus, the compression level may vary depending on the patient's medical condition, the position of the limb or body portion relative to the heart, and how active the patient is in moving and using their muscles.

In selected embodiments, the baseline compression of certain compression garments and the end-stretch thereof may be somewhat subjective. For example, a ninety-year-old patient may apply a compression garment with less tension than a young athlete. Furthermore, the end-stretch may be felt or perceived as a deceleration in the material as it is pulled. The velocity with which a material is initially pulled may, to some degree, affect the perception of where the material locks out and quits stretching. Accordingly, there may be challenges in applying a compression garment at or near maximal stretch, where the best garment function may reside.

It may be risky to apply a compression garment to a post-surgical or obtunded patient or patients with severe polyneuropathy such as from diabetes, or patients with underlying peripheral arterial disease. Caregivers are often family members or hospital or nursing home staff. Often there is little training available for these family members or staff in application of a compression garment safely and therapeutically.

If a compression garment is applied too tight (e.g., with a baseline compression that is too high), pressure necrosis can occur to underlying tissues. Post-surgical patients who are sedated with anesthesia or pain medicines or other patients with hypotension may have less perfusion pressure of arterial blood to their body and thus are at higher risk of pressure-necrosis-type damage from higher compression levels. These patients may require less therapeutic baseline resting compression, but would still benefit from a compression garment applied at or near end-stretch to therapeutically reduce swelling and reduce risk of it worsening.

Referring to FIGS. 1-5, a therapeutic system 10 in accordance with the present invention may include a compression garment 12 and one or more gauges 14. A compression garment 12 may be constructed to deliver a desired compression profile to a patient. The compression profile may be uniform (substantially uniform compression across a limb or portion of a limb), gradient (decreasing compression from distal to proximal on a limb or portion of a limb), progressive (increasing compression from distal to proximal on a limb or portion of a limb), or a combination or sub-combination thereof. For example, in a progressive compression profile, there may be 30-40 mmHg compression in the calf area, but only 20-30 mmHg compression in the ankle area.

A compression garment 12 may have any suitable configuration, construction, or combination thereof. Various compression garment features, materials, fabrics, physical properties, combinations, methods, bands, attachment mechanisms or closures, liners, padding, shapes, dimensions, and the like are disclosed in U.S. Patent App. Publication No. 2005/0209545 A1, U.S. Patent App. Publication No. 2007/0179421 A1, U.S. Patent App. Publication No. 2010/0056973 A1, and U.S. Patent App. Publication No. 2010/0312160 A1, each of which is hereby incorporated by reference. Any suitable embodiment, sub-combination of an embodiment, combination of embodiments, and the like of such garments, features, materials, methods, etc. may be used to produce a compression garment 12 in accordance with the present invention.

A gauge 14 in accordance with the present invention may communicate to a user (e.g., a patient, caregiver, medical professional, etc.) when a compression garment 12 (or some portion thereof) has been stretched a proper amount. This proper amount of stretch may correspond to a desired or prescribed compression. Accordingly, when a gauge 14 indicates that a compression garment 12 has been stretched a proper amount, a user may know that the compression garment will deliver the desired or prescribed compression.

For example, when applied, a compression garment 12 may encircle a limb of a patient and secure to itself. During a donning process, a user may apply a tensile force to stretch the compression garment 12 or a portion thereof. Accordingly, a user may stretch a compression garment 12 or a portion thereof until a corresponding gauge 14 indicates that the proper amount of stretch has been reached. Then, while maintaining that proper amount of stretch, the user may wrap the compression garment 12 or portion thereof about the limb and secure it in place (e.g., secure it to an opposing portion of the compression garment 12 using one or more attachment mechanisms 16).

A gauge 14 in accordance with the present invention may be applied on various surfaces of a compression garment 12. For example, in selected embodiments, a gauge 14 may be applied on an exterior surface of a compression garment 12. Such a placement may be helpful to a caregiver or medical professional who is applying the compression garment 12 to another person. In other embodiments, a gauge 14 may be applied to an interior surface of a compression garment 12. This may enable a user to read the gauge 14 as he or she stretches the compression garment 12 away from a limb. Such a placement may be helpful to a patient that is unable to obtain a good view of his or her legs or the like. In still other embodiments, at least one gauge 14 may be applied to each of the interior and exterior surfaces of a compression garment 12.

Proper compression may correspond to any suitable stretch or percent elongation of a compression garment 12 or a portion thereof. Accordingly, one or more gauges 14 of a compression garment 12 may be "tuned" to (e.g., indicate on) whatever stretch or percent elongation produces the proper or desired (e.g., prescribed) compression.

For example, in certain embodiments, one or more gauges 14 may be applied to a compression garment 12 that comprises or is formed of short stretch material. Short stretch material may reach or hit at an end stretch after an elongation in the range of about 15% to about 100%. For example, in certain embodiments, the repeatable and elastic elongation of a short-stretch fabric may be in the range of about 20% to about 40%.

End stretch may be defined as the percentage of stretch present when a user feels a distinct or abrupt increase in the resistance of the material to further stretching. This may be considered to be a user-appreciable end stretch. Alternatively, end stretch may be more objectively defined. For example, end stretch may correspond to a percentage of stretch when a standardized sample of material is stretched with a standard load. In selected embodiments, end stretch may correspond to a percentage of stretch after 10 N/cm is applied to the material, wherein the centimeter component may correspond to a characteristic dimension (e.g., length of material, width of material, or the like)

In selected situations, there may be medical or performance advantages to applying a compression garment 12 to a patient at or near end stretch. Unfortunately, there may be a lack of precision in the ability of different users to determine exactly when a compression garment 12 or portion thereof has reached end stretch. Accordingly, in certain embodiments, one or more gauges 14 may be tuned to end stretch (e.g., indicate that a proper stretch has been reached when the compression garment 12 or a portion thereof has been stretched to a point at or near end stretch).

For example, certain short stretch materials may have an end stretch that is less appreciable (e.g., less abrupt). Accordingly, the end stretch of that short stretch material may be harder to detect or judge. Moreover, different users may judge the end stretch to be at different percentages of elongation. Accordingly, one or more gauges 14 may promote consistent application of a compression garment 12 comprising short stretch material at or near end stretch across different uses and users.

That is, for a given short stretch material, different users may feel they have reached an appreciable end stretch after an elongation somewhere in a particular range (e.g., a range of 30% to 40%). Some users may feel that they have stretched the material to an appreciable end stretch at a lower end of that range (e.g., at 30% elongation). Other users may feel that they have stretched the material to an appreciable end stretch at a higher end of that range (e.g., at 40% elongation). Still other users may feel that they have stretched the material to an appreciable end stretch when they reach a percent elongation that is somewhere within that range (e.g., at somewhere between 30% and 40% elongation).

Accordingly, in such situations a particular percentage of elongation may be selected as the end stretch. This particular percentage may be considered to be the official, nominal, or optimal elongation for end stretch. For example, in the example set forth above, an average or median elongation of 35% may be selected. Thereafter, one or more gauges 14 may be tuned to the official, nominal, or optimal elongation for end stretch (e.g., tuned to 35% elongation). Accordingly, upon stretching the material to the official, nominal, or optimal elongation, the gauge 14 may indicate that the compression garment 12 is properly stretched. In this manner, the user may obtain or establish a better or more precise feel for end stretch.

In certain embodiments, one or more gauges 14 may be training tools. For example, once this better or more precise feel has been obtained or established, a user may stop referencing the one or more gauges 14. Alternatively, one or more gauges 14 may be used with the end stretch to give the user added confidence that the compression garment 12 has been applied in a manner that will deliver the prescribed compression.

In selected embodiments, a gauge 14 may communicate with a user via the visual senses of the user. For example, in certain embodiments, a gauge 14 may comprise one or more features 18 applied (e.g., printed) on a compression garment 12. Accordingly, as the compression garment 12 stretches, the one or more features 18 may be stretched and distorted as well. When this stretching or distortion of the one or more features 18 reaches a particular amount, a user may know that the compression garment 12 has been stretched a proper amount. Thus, a feature 18 may be tuned to provide a desired or prescribed compression level or compression within a desired or prescribed range.

A proper amount of stretching or distortion of the one or more features 18 may be recognized in any suitable manner. For example, in selected embodiments, the one or more features 18 may be stretched or distorted until a particular separation or spacing corresponding thereto reaches a particular value. This value may be verified by measuring the separation or spacing using a ruler or other reference. For example, in certain embodiments, a feature 18 may comprise two lines or hash marks spaced from one another. Such a compression garment 12 may be properly stretched when the value (i.e., the distance between the two lines or hash marks) is equal to one inch on a ruler.

In other embodiments, a compression garment 12 may be properly stretched when the value is equal to some other reference distance. For example, a compression garment 12 may be properly stretched when the value is equal to a size (e.g., height and/or width) or shape of a manufacturer's logo on a key fob or tag supplied to the patient or user. In selected embodiments, such a fob, tag, or the like may comprise or include a plastic square logo or other paper or plastic shape that is the same size as a properly stretched gauge 14 or feature 18 thereof.

Alternatively, this value may be verified visually by the user comparing the value to some other dimension of the compression garment 12, material, or one or more features 18. For example, in an unstretched or undistorted condition, a feature 18 may comprise a rectangle. In general, the rectangle may be oriented such that the stretching of the compression garment 12 during an application or donning process produces an increase in width with little to no change in the length thereof. Accordingly, as the compression garment 12 is stretched and applied or donned, the rectangle may increase in width until it becomes a square. The point at which the rectangle becomes a square may correspond to the correct value, which in turn may correspond to the proper amount of stretch.

Within acceptable accuracy, a user may determine the point at which the rectangle becomes a square. The user may simply judge or determine with his or her sight and mind the point at which a width of the rectangle becomes substantially equal to the length of the rectangle. Accordingly, the user may also, with acceptable accuracy, don or apply a compression garment 12 in accordance with the present invention with the desired or prescribed level of compression.

In selected embodiments, a compression garment 12 may include one or more other features 18 that do not involve the rectangle to square transition, but that can also be verified visually by the user. For example, in an unstretched or undistorted condition, one or more features 18 may comprise an ellipse, star, isosceles triangle, or the like. In general, each such shape may be oriented such that the stretching of the compression garment during an application or donning process produces an increase in width with little to no change in the length thereof. Accordingly, as the compression garment 12 is stretched, the ellipse, star, isosceles triangle, or the like may increase in width until it obtains the shape of a circle, regular star polygon, equilateral triangle, or the like, respectively. The point of this transition may correspond to the correct value, which in turn may correspond to the proper amount of stretch and, therefore, the proper amount of compression.

In selected embodiments, a gauge 14 may communicate with a user via the tactile senses of the user. For example, in certain embodiments, a gauge 14 may comprise a feature 18 comprising a plurality of tactile objects 20 applied on a compression garment 12 (e.g., a plurality of raised objects pinned, sewed, bonded, or otherwise incorporated into a compression garment 12). Accordingly, as the compression garment 12 stretches, the various distances between the various tactile objects 20 may be stretched and distorted as well. When this stretching or distortion reaches a particular amount, a user may know that the compression garment 12 has been stretched a proper amount. Thus, the feature 18 comprising a plurality of tactile objects 20 may be tuned to provide a desired or prescribed compression level or compression within a desired or prescribed range.

For example, in an unstretched or undistorted condition, a feature 18 may four tactile objects 20 forming the corners of a rectangle. In general, the rectangle may be oriented such that the stretching of the compression garment 12 during an application or donning process produces an increase in width-wise distance between certain tactile objects 20 and little to no change in the length-wise distance between certain tactile objects 20. Accordingly, as the compression garment 12 is stretched and applied or donned, the width-wise distances may increase until they are substantially equal to the length-wise distances.

The point at which the width-wise distances are substantially equal to the length-wise distances may correspond to the proper amount of stretch. This point may be discerned by a user by touch. Accordingly, the user need not be able see the compression garment 12 in order to discern a proper usage thereof. For example, the tactile objects 20 may be sized and positioned such that a user may pass a finger tip there between and touch a tactile object 20 on each side. Accordingly, with a finger tip, a user may judge whether one distance (e.g., a width-wide or horizontal distance) between two tactile objects 20 is substantially equal to another distance (e.g., a length-wise or vertical distance) between two objects 20.

Alternatively, in selected embodiments, a feature 18 may comprise four or more tactile objects 20 positioned around a perimeter of an ellipse and one tactile object 20 at the "center" of the ellipse. In general, the ellipse may be oriented such that the stretching of the compression garment 12 during an application or donning process produces an increase in width-wise distance between certain tactile objects 20 and little to no change in the length-wise distance between certain tactile objects 20. Accordingly, as the compression garment 12 is stretched and applied or donned, the width-wise distances may increase until they are substantially equal to the length-wise distances.

The tactile objects 20 may be sized and positioned such that a user may pass a finger tip around the interior of the ellipse and sense (e.g., with that finger tip) the spacing between the center tactile object 20 and the tactile objects 20 positioned on the perimeter of the ellipse. Accordingly, with a finger tip, a user may judge whether the center tactile object 20 is equidistant from the various surrounding tactile objects 20. If it is, the user may know that the stretching has transitioned the ellipse into a circle and that a proper amount of stretching has been applied.

In selected embodiments, a feature 18 may be visual as well as tactile. Accordingly, it may work for users operating on sight, touch, or both. For example, a plurality of tactile objects 20 may form the vertices of a rectangle. Accordingly, the sight and mind of the user may determine when the rectangle outlined by the tactile objects 20 becomes a square. In selected embodiments, the tactile objects 20 may be positioned on one or more lines or curves (e.g., one or more lines or curves printed onto a compression garment 12) forming a particular shape. Such lines and curves may help a user better determine by sight when the transition (e.g., to a square, circle, or the like) takes place.

In certain embodiments, a gauge 14 may comprise a continuous feature 18 or a feature 18 that extends continuously for some distance. For example, in selected embodiments, a feature 18 may comprise a rectangular wave form or the like. Accordingly, a proper amount of stretch may correspond to the point where the rectangular wave form becomes a square wave form or the like.

In other embodiments, a proper level of stretch and compression may be reached when there is a color change on a gauge 14. For example, in selected embodiments, a gauge 14 may be electronic gauge. Such a gauge 14 may measure a compression level and provide a visual indicator (e.g., color change, digital compression readout, or LED color bars) indicative of the compression being applied by a garment 12. An electronic gauge 14 may be applied to various portions of a garment 12. Alternatively, an electronic gauge 14 may be used sequentially on different portions of a garment 12 as they are tensioned and applied. In embodiments where a gauge 14 is electronic and selectively detachable as the user dons a garment 12, the gauge 14 may be reusable (e.g., suitable for use on different garments 12).

An electronic gauge 14 may communicate directly with a patient or caregiver or may use wireless communication (e.g., WiFi, Bluetooth, infrared signals, or the like) to communicate with an "app" or the like on a smart watch or mobile phone. In selected embodiments, an electronic gauge 14 may employ audible signals such as a beep, series of beeps, or sound frequency to indicate if the user is applying a portion of a garment 12 with too little or too much compression.

In certain embodiments, an electronic gauge 14 may comprise or include two fiducial markers on a portion of a garment 12. When the garment 12 is stretched, the distance between the fiducial markers may be measured electronically. In selected embodiments, such markers may include a fragment of magnetic or ferrous material or may conduct electricity therethrough. For example, the markers may include a resistor (e.g., linear potentiometer, strain gauge) or an inductor whose resistance or inductance changes as a corresponding portion of garment 12 is stretched. Accordingly, the change in resistance, inductance, or the like may be calibrated to the corresponding compression.

In selected embodiments, an electronic gauge 14 may selectively attach and detach from a portion of a garment 12 at a top or bottom thereof or both or may snap into place along a portion of a garment 12. For example, in selected embodiments, an electronic gauge 14 may be magnetically secured in place. In such embodiments, the magnet material may also participate in the measurement of displacement (which, as discussed above, can be correlated to compression). For example, a thin film magnet may be hold a gauge 14 in place and also change in some other property (e.g., electrical resistance, inductance, etc.) with stretching of the garment 12. Thus, a gauge 14 may be lightweight, portable, and easy for all patients to use.

In a therapeutic system 10 in accordance with the present invention, one or more gauges 14 may be applied to a compression garment 12. Accordingly, the compression produced by various portions of a compression garment 12 may be accurately controlled. For example, in selected embodiments, a compression garment 12 may comprise a plurality of bands 22. Each band 22 of the plurality of bands 22 may include at least one gauge 14 to enable a user to properly apply that band 22 using a corresponding attachment mechanism 16.

Alternatively, a compression garment 12 may be more continuous (e.g., comprise a substantially continuous sheet 24 or a sheet with tabs 26 formed at an edge thereof) such that stretching of one portion of the compression garment 12 may induce at least some stretching in one or more adjacent portions of the compression garment 12. Accordingly, various portions (e.g., edges, center portions) of a compression garment 12 may each have a gauge 14 applied thereto so that each such portion may be properly applied (e.g., using one or more attachment mechanism 16) to a patient.

A gauge 14 may be oriented to match an intended direction of stretch of a corresponding portion of a compression garment 12 (e.g., oriented to match the vector force that will be applied thereto). Not all portions of a compression garment 12 may be stretched or tensioned in the same direction. Accordingly, certain gauges 14 may be angled with respect to (e.g., oriented differently than) other gauges 14.

For example, to accommodate a lobule on the limb of a patient, a first portion of a compression garment 12 (e.g., one or more first bands, tabs, or portions) may be positioned or stretched to lift the lobule, while a second portion of the compression garment 12 (e.g., one or more second bands, tabs, or portions) may be positioned or stretched to compression the lobule. Accordingly, one or more gauges 14 corresponding to the first portion may be oriented in a first direction to gauge the compression corresponding thereto, while one or more gauges 14 corresponding to the second portion may be oriented in a second direction, distinct from (e.g., non-parallel with respect to) the first direction, to gauge the compression corresponding thereto.

Figure 6:
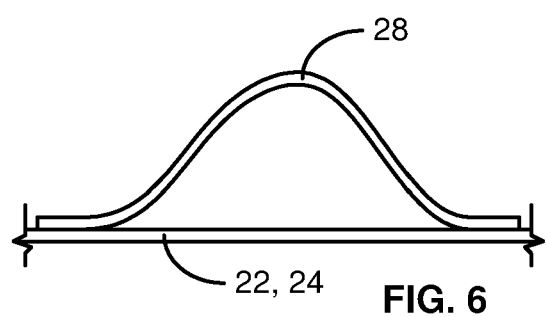
FIG. 6 is a schematic diagram illustrating an edge view of a portion of one embodiment of a therapeutic system in accordance with the present invention with the limiter of the compression gauge in slack position.
Figure 7:
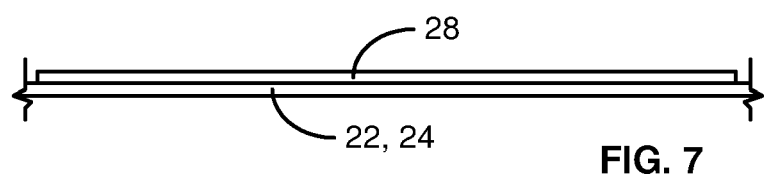
FIG. 7 is a schematic diagram of an edge view of the therapeutic system of FIG. 6 with a portion of the compression garment being stretched to the point where the slack in the limiter has been consumed.

Referring to FIGS. 6 and 7, in certain embodiments, a gauge 14 may comprise a limiter 28. Accordingly, a gauge 14 may communicate with a user via the tactile or visual senses of the user through the use of a limiter 28. A limiter 28 may include a substantially inextensible string, cord, strip, strap, or the like that limits the amount of stretch that may be applied to a compression garment 12 or a portion or segment thereof.

For example, when a corresponding portion of a compression garment 12 in an unstretched or undistorted condition, a limiter 28 may have slack therein. Accordingly, as the compression garment 12 is stretched, the slack of the limiter 28 may be consumed until further stretching or elongation of a corresponding portion or segment of the compression garment 12 would require stretching or elongation of the limiter 28.

A limiter 28 may have any suitable length. For example, in certain embodiments, a limiter 28 may sized to substantially encircle a limb of a patient. Alternatively, a limiter 28 may be much shorter. For example, a limiter 28 may be applied to or cover a relatively short portion of segment of compression garment 12 or band thereof (e.g., a one to three inch (5.1 cm to 7.6 cm) portion of a compression garment 12). In selected embodiments, the stretch of that relatively short portion or segment may be representative of the stretch that is occurring over a larger portion of the compression garment 12.

Since a limiter 28 may be substantially inextensible, it may resist elongation and provide an "end stretch" (e.g., a user-appreciable and abrupt end to the stretching) to the compression garment 12 or a corresponding portion thereof. The point may correspond to the correct value, which in turn may correspond to the proper amount of stretch and, therefore, the proper amount of compression. In certain embodiments, the point at which the slack of a limiter 28 has been consumed may be felt by a user. Accordingly, user may know when to cease further stretching of the compression garment 12 or corresponding portion or segment thereof.

Alternatively, or in addition thereto, a limiter 28 may provide a visual indicator. Accordingly, when a user sees that the slack of a limiter 28 has been consumed, the user may know to cease further stretching of the compression garment 12 or corresponding portion or segment thereof. In selected embodiments, when only a visual indicator (and no tactile indicator) is needed, a limiter 28 may be formed of a material that exhibits user appreciable elasticity or stretch. In such embodiments, the user need only stretch the compression garment or corresponding portion or segment thereof until the slack of the limiter 28 has been consumed.

In selected embodiments, a limiter 28 may be about 3 to 5 cm long and be applied to a band 22 that is about 30 cm long. The limiter 28 may be the width of the band 22 or just a small strap (e.g., a 1 cm strap) of fabric, flat ribbon, plastic, or other material. The limiter 28 may have little to no elasticity. The limiter 28 may be positioned or located at a top inside surface of the band 22. There may be just one limiter 28 on the end of the band 22 or there may be one limiter 28 on each end of the band 22.

A user may stretch the band 22 until he or she sees that the limiter 28 was just taunt with the band 22, which would indicate to the user that the correct therapeutic compression had been achieved. In such embodiments, the band 22 may be or exhibit limited linear stretch. In other embodiments, a limiter 28 may include electronics be a more complex system. An electronic limiter 28 may alternatively include piezoresistive, inductive, conductive, resistive, or other electronic measurements to help verify and relay to the user the compression reading, that the garment was applied therapeutically, or other information either directly or through a smart watch or phone.

In embodiments where a limiter 28 extends the length of the corresponding band 22, the combination of an elastic compression band 22 and the relatively inelastic limiter 28 may combine and function together as a short stretch band. Accordingly, systems 10 in accordance with the present invention may include a garment 12 with at least one band 22, wherein the at least one band 22 comprises a limiter 28 and an elastic material. The combination of the limiter 28 and the elastic material enables the resulting structure to function as a short-stretch band 22, wherein the band 22, once applied with enough tension to fully stretch the limiter 28, may provide a resting compression level to a limb circumference of one of 20-30 mmHg, 30-40 mmHg, 40-50 mmHg, or another standard.

A limiter 28 may be connected to a compression garment 12 in any suitable manner. For example, a limiter 28 may connect to a compression garment 12 at opposite ends of the limiter 28. Between those ends, the limiter 28 may be free to move with respect to the compression garment 12. In certain embodiments, a limiter 28 may extend between two or more layers of a material forming a compression garment 12. Accordingly, a limiter 28 may be hidden from view. Alternatively, a limiter 28 may extend partially or substantially exterior to a corresponding compression garment 12.

In selected embodiments, one or both ends of a limiter 28 may connected to a compression garment 12 via a releasable connection (e.g., via a hook-and-loop connection). Accordingly, the slack in a limiter 28 may be selected by adjusting the position of one or more ends of the limiter 28 with respect to a compression garment 12. Such adjusting may enable tuning of the limiter 28 to a particular stretch and, as a result, to a particular compression level.

In selected embodiments, various locations for securing one or more ends of a limiter 28 may be marked on a compression garment 12. For example, one marking may show where to securing an end of a limiter 28 to obtain a first compression level, while another marking may show where to secure that end of the limiter 28 to obtain a second compression level, different from the first compression level.

In another embodiment, the limiter functions to limit or reduce stretch of the applied compression band around the calf muscle. In this embodiment, the garment consists of multiple compression bands, wherein the garment includes a limiter located over the posterior calf area, such that the limiter functions to improve or maximize the calf muscle pump when the limb is active/moving.

In certain embodiments, a gauge 14 may comprise a system (e.g., a piece of material) whose properties change with elongation. The system may be attached to a compression garment 12 or portion thereof to move and stretch therewith. Alternatively, the system may interrupt a portion of a compression garment 12 such that the tension applied to a compression garment 12 or portion thereof passes through the system.

Such a system may change in any suitable way when stressed or stretched. For example, the system may change color with the stress applied thereto. Accordingly, a particular color may be correlated with a particular tension (and, hence, elongation) of the compression garment 12 or a portion thereof. A user may then stretch the compression garment 12 or portion thereof until the system reaches a particular color. The proper color may be confirmed with a simple judgment by the user or by comparison to a particular standard (e.g., a particular swatch of color).

Alternatively, the system may change texture with the stretch applied thereto. For example, in an unloaded underloaded situation, the system may have a rippled or rough texture. However, when properly stretched, the system may adopt a smooth texture. Alternatively, in an unloaded underloaded situation, the system may have a smooth texture. However, when properly stretched, the system may adopt a rough or quilled texture. This change in texture may be correlated with a proper or desired tension or elongation of the compression garment 12 or a portion thereof.

In selected embodiments, a gauge 14 may comprise a single feature 18 or a plurality of features 18. For example, a gauge 14 may include multiples of the same feature 18. Alternatively, a gauge 14 may include a plurality of different features 18. The various features 18 corresponding to the same gauge 14 may all be tuned to provide the same compression or different features 18 may be tuned to provide different compression.

For example, a first feature 18 may be tuned to provide compression within one range (e.g., 8-15 mm Hg, 15-20 mm Hg, 20-30 mm Hg, 30-40 mm Hg, 40-50 mm Hg, or higher), while one or more other features 18 are tuned to provide compression within one or more other ranges (e.g., 8-15 mm Hg, 15-20 mm Hg, 20-30 mm Hg, 30-40 mm Hg, 40-50 mm Hg, or higher). The features 18 corresponding to the different ranges may be distinguished by size (e.g., smaller rectangle for lower compression range, larger rectangle for higher compression range), shape (ellipse for lower compression range, rectangle for higher compression range), color (green rectangle for lower compression range, red rectangle for higher compression range), or the like or a combination or sub-combination thereof.

In selected embodiments, the proper or desired amount of stretch may be different for different portions of a compression garment 12. Accordingly, the starting (e.g., neutral or undistorted) dimensions of the features 18 or limiters 28 of various gauges 14 may be different at different portions of a compression garment 12. Such variability among the gauges 14 of a compression garment 12 may provide a mechanism for efficiently and effectively dealing with the relationship between sub-garment pressure and limb circumference. Alternatively, or in combination therewith, it may provide a mechanism for efficiently and effectively dealing with different widths of bands within a compression garment 12, different overlap of bands within a compression garment 12, different fabrics or materials within a compression garment 12, the presence or absence of padding under a compression garment 12 or one or more portions thereof, or the like or combinations or sub-combinations thereof.

For example, for a given stretch distance in a compression garment 12, sub-garment pressure will vary inversely and non-linearly with circumference of a limb of a patient. This inverse and non-linear relationship may be difficult for user to understand and accommodate. Moreover, the situation can be further complicated by the need to apply a desired or prescribed compression profile (e.g., uniform, gradient, progressive, or a combination or sub-combination thereof) to a limb.

Accordingly, in selected embodiments in accordance with the present invention, solutions for this relationship and for the desired or prescribed compression profile may be built into the starting dimensions of the features 18 or limiters 28 of various gauges 14. The end result is that a user need only stretch a compression garment 12 or portion thereof until a gauge 14 corresponding thereto indicates that the proper stretch has been reached, then secure the compression garment 12 in place at that level of stretch.

Alternatively, or in combination therewith, the starting dimensions of the features 18 or limiters 28 of various gauges 14 may be different at different portions of a compression garment 12 to accommodate or adjust for different widths of bands, different overlap of bands, different fabrics or materials, or the like within a compression garment 12. Thus, a significant amount of complexity and fine tuning may be built into a compression garment 12 without requiring that a user understand it. The complexity may be transparent to the user. The user need only stretch each portion of a compression garment 12 until a corresponding gauge 14 indicates that the proper amount of stretch has been obtained, then secure the compression garment 12 in place at that level of stretch.

For example, in certain embodiments, a gauge 14 may be or comprise a rectangle that becomes a square when a corresponding band 22 is stretched to provide an appropriate target compression around a given limb circumference, or an appropriate target compression range around a given limb circumference range. In selected embodiments, bands 22 may be about 7 cm to about 25 cm in width (e.g., measured from a distal edge to a proximal edge). For example, bands 22 may be about 8 cm to about 12 cm in width for lower limbs and about 12 cm to about 25 cm in width for upper limb (e.g., thigh) areas. Such a gauge 14 may include a rectangle about 3 cm to about 8 cm tall that may become a 3 by 3 cm to an 8 by 8 cm square when a corresponding band 22 is stretched to provide the appropriate compression level to a known limb circumference (or an appropriate compression range for a known limb circumference range). In other embodiments, gauge 14 may include a feature 18 of any size from about 1 cm by 1 cm to a full width of a corresponding band 22.

In certain embodiments, one or more bands 22 of a garment 10 may be at or near end stretch (e.g., at or within 5% of a user-appreciable end stretch) when applied around a posterior calf muscle area. This amount of stretching may coincide with the tuning of a corresponding gauge 14 (e.g., a corresponding rectangle becoming a square) and provide therapeutic compression and with a maximal augmentation of the calf muscle pump. The band 22 may also be designed to be applied at a little bit less than end stretch when applied around the anterior ankle area or other bony body limb areas. This may reduce the risk of pressure necrosis to the anterior tibialis tendon, other bony areas, or areas of the body with little subcutaneous fat.

The anterior tibialis tendon is often prominent when the foot is flexed at 90 degrees to the lower limb and may experience pressure damage caused by compression bandages and garments. Accordingly, bands 22 may be applied with some remaining stretch when applied with correct therapeutic compression for some body parts. For example, one or more gauges 14 on one or more bands 22 corresponding to an anterior tibialis (or other sensitive area) may be tuned to leave about 10-15% remaining stretch (i.e., before an end stretch is reached) when applied with the correct compression, in order to enable the one or more bands 22 to give as the ankle is flexed.

Thus, a therapeutic system 10 in accordance with the present invention may have one or more bands 22 (e.g., one or more bands 22 corresponding to a calf area) tuned to end stretch and one or more bands 22 tuned to leave about 10 to about 15% stretch in other areas (e.g., anterior tibialis areas, boney areas, areas with little subcutaneous fat). Such a system 10 may provide optimal compression (e.g., maximize augmentation of the calf muscle pump) without producing pressure necrosis or discomfort over the anterior tibialis tendon or boney or sensitive areas.

Accordingly, a system 10 in accordance with the present invention may include a garment 12 with at least one band 22, wherein the band 22 has a gauge 14 thereon to apply a known resting compression to an underlying body circumference when the band 22 is not applied at or near full end stretch. A system 10 in accordance with the present invention may also include a garment 12 with at least two bands 22, wherein one or more bands 22 have a gauge 14 thereon to apply a known resting compression to an underlying body circumference when the band 22 is not applied at or near full end stretch and one or more bands 22 have a gauge 14 thereon to apply the proper compression when the bands 22 are pulled at or near end-stretch.

Example 1

In a first hypothetical or exemplary embodiment, a garment 12 may comprise one or more bands 22 that are about 9 cm wide and provide about 20 mmHg to about 30 mmHg of compression when stretched 20% (i.e., stretch to 120% of a pre-stretched or neutral length) and applied to an ankle circumference of about 20 cm to about 24 cm. Such a garment 12 may be suitable for treating a patient with mild chronic venous insufficiency. The garment 12 may have applied thereto a feature 18 comprising a 4 cm by 5 cm rectangle that becomes a 5 cm by 5 cm square when stretched 20% stretch.

Example 2

In a second hypothetical or exemplary embodiment, a garment 12 may comprise one or more bands 22 that are about 9 cm wide and provide about 20 mmHg to about 30 mmHg of compression when applied to an ankle circumference of about 25 cm to about 30 cm. This circumference is larger than the circumference in Example 1. Accordingly, to apply the same 20-30 mmHg of compression, the rectangle will need to be less wide in its unstretched configuration. For example, the feature 18 may be a 3.9 cm by 5 cm rectangle that becomes a 5 cm by 5 cm square when the proper amount of stretch has been reached.

Thus, by changing the initial geometry of a feature 18, a system 10 may be tuned to a particular patient or a particular range of patient sizes. Such variability enables systems 10 in accordance with the present invention to provide or support a product line of garments 12 comprising multiple compression bands 22, wherein each size range of the product line has a different compression gauge 14 to provide the correct compression range for the limb sizes in that range.

Example 3

In a third hypothetical or exemplary embodiment, a garment 12 may comprise one or more bands 22 that are about 9 cm wide and provide about 40 mmHg to about 50 mmHg of compression when stretched 30% (i.e., stretch to 130% of a pre-stretched or neutral length) and applied to an ankle circumference of about 20 cm to about 24 cm. Such a garment 12 may be suitable for treating a patient with severe chronic venous insufficiency with ulceration. The garment 12 may have applied thereto a feature 18 comprising a 3.5 cm by 5 cm rectangle that becomes a 5 cm by 5 cm square when stretched 30%.

The material of the bands 22 in Example 3 may be the same as the material of the bands 22 in Example 1. Thus, by selecting an appropriate initial, neutral or unstretched dimension of the gauge 14 (e.g., the rectangle), the same garment 12 may be used to provide different ranges of compression. For example, by selecting an appropriate initial, neutral or unstretched dimension of the gauge 14, a particular garment 12 may be tuned to compression of 15-20 mmHg, 20-30 mmHg, 30-40 mmHg, and 40-50 mmHg. A particular garment 12 may also be tuned to other compression ranges falling within the Raul standard, French standard, English standard, or any other compression standard or a custom compression standard.

Example 4

In a fourth hypothetical or exemplary embodiment, a garment 12 may comprise one or more bands 22 that are tuned to different amounts of stretch to provide a graduated compression profile. The patient for this example may have a thin leg that is basically cylindrical in shape from the ankle to the top of the calf. This portion of the leg may be about 20 cm in circumference all the way up. In this example, the one or more bands 22 may be tuned via one or more gauges 14 to provide a graduated compression profile with the most compression at the ankle. For example, the graduated compression profile may have 25% less compression at the calf than at the ankle. In other embodiments, the graduated compression profile may have 15% less compression at the calf than at the ankle. In still other embodiments, a custom compression profile (e.g., a profile suitable for accommodating a large lobule requiring greater compression), or a progressive compression profile (e.g., 30-40 mmHg of compression to the calf and 20-30 mmHg of compression to the ankle area) may be tuned.

To create the graduated compression profile specified in this example, the garment 12 may have applied thereto a feature 18 comprising a 3.85 cm by 5 cm rectangle that becomes a 5 cm by 5 cm square when stretched 23%. Such a feature 18 may be applied to one or more bands 22 corresponding to an ankle area and produce about 30 mmHg of compression. The garment 12 may further have applied thereto a feature 18 comprising a 4.025 cm by 5 cm rectangle that becomes a 5 cm by 5 cm square when stretched 19.5%. Such a feature 18 may be applied to one or more bands 22 corresponding to a calf area and produce about 22.5 mmHg of compression.

Accordingly, different bands 22 along the length of a limb may have gauges 14 of different initial, neutral, or unstretched dimensions. Moreover, initial, neutral, or unstretched dimensions may be selected to provide, for a particular limb geometry, a compression profile that is graduated, progressive, or a custom.

Example 5

A resting compression level may be the compression level of the garment applied to a limb in a supine position (i.e., no gravity effects and no calf muscle augmentation because the limb is inactive). The resting compression level applied to a limb may be a function of the width of one or more bands 22, the tension with which the one or more bands 22 is applied, the number or degree of overlap of the one or more bands 22, the force of the one or more bands 22 over time, the limb circumference to which the garment 12 is applied, and even the friction of each band 22 on any underlying band 22. Accordingly, in a fifth hypothetical or exemplary embodiment, a garment 12 may comprise one or more bands 22 that are tuned to different overlap of amounts of two or more bands 22.

In this example, two garments 12 may be considered. A first garment 12 may have two or more bands 22 that alternatingly extend from the sides with little overlap (i.e., an alternating band design). A second garment 12 may have a 50% band overlap (i.e., a 50% overlap design) where each band 22 overlaps 50% of an adjacent underlying band 22 all the way up (e.g., all the way up a lower portion of a limb from an ankle to just above a calf muscle).

In the alternating band design where a single band 22 is at each level, the garment 12 may provide 30 mmHg of compression when applied to a calf area. In this example, the band 22 may stretch 30% (i.e., 130% of an unstretched length) to provide 30 mmHg of compression to a calf circumference. Therefore, with the alternating band design, the garment 12 may have applied thereto a feature 18 comprising a 3.5 cm by 5 cm rectangle that becomes a 5 cm by 5 cm square when stretched 30%.

In the 50% overlap design, each band 22 may only need to provide half the force because there are two bands 22 all along the covered portion of the limb. In real applications, this may not be the case due to friction between the bands 22 and other physics principles. Accordingly, in certain situations, each band 22 may need to provide (e.g., be rated and/or tuned to provide) more than 50% of the desired compression. In this example, each band 22 may be stretched 25% and, when combined with one or more adjacent bands 22, may apply the same compression level of 30 mmHg to the same calf circumference. Therefore, with the 50% overlap design, the garment 12 may have applied thereto multiple features 18 comprising a 3.75 cm by 5 cm rectangle that becomes a 5 cm by 5 cm square when stretched 25%.

Example 6

In a sixth hypothetical or exemplary embodiment, a garment 12 may comprise one or more bands 22 that are 9 cm wide and one or more bands 22 that are 18 cm wide. In this example, a single layer of bands 22 may be applied to the limb. Therefore, if a band 22 that is 9 cm wide is applied to a limb circumference using a force and a band 22 that is 18 cm wide is applied to the same limb circumference using the same force, the wider band 22 may provide 50% of the compression to the limb as compared to the narrower band 22. Accordingly, if the goal is to provide the same compression level to the underling limb, the wider band 22 may, theoretically, be applied with about twice the force as the narrower band 22.

Therefore, the one or more bands 22 having a width of 9 cm may have applied thereto one or more features 18 comprising a 4 cm by 5 cm rectangle that becomes a 5 cm by 5 cm square when stretched 20%. Using the same compression material, the one or more bands 22 having a width of 18 cm may have applied thereto one or more features 18 comprising a 3.825 cm by 5 cm rectangle that becomes a 5 cm by 5 cm square when stretched 23.5% (a percentage of stretch that, in this example, corresponds to twice the force). Accordingly, a system 10 in accordance with the present invention may include one or more gauges 14 that are sized to address differences in band width.

Example 7

In a seventh hypothetical or exemplary embodiment, a system 10 in accordance with the present invention may include one or more gauges 14 taking into account an effect of padding positioned under the garment 12. For example, a first garment 12 may be applied over a thin, sock-type liner, while a second garment 12 is applied over a thin layer of foam or spacer fabric. For the second garment 12, more compression must be applied in order to provide the same sub-bandage pressure as the first garment 12.

Accordingly, a garment 12 may comprise one or more bands 22 that are about 9 cm wide and provide about 40 mmHg of compression when stretched 20% (i.e., stretched to 120% of a pre-stretched or neutral length) and applied to an ankle circumference. Therefore, when the garment 12 is to be used without any padding, the one or more bands 22 may have applied thereto one or more features 18 comprising a 4 cm by 5 cm rectangle that becomes a 5 cm by 5 cm square when stretched 20%. However, when the garment 12 is to be used with a thin layer of foam or spacer fabric padding, the one or more bands 22 may have applied thereto one or more features 18 comprising a 3.8 cm by 5 cm rectangle that becomes a 5 cm by 5 cm square when stretched 24%. Accordingly, a system 10 in accordance with the present invention may include one or more gauges 14 that are sized to address differences in padding or the presence or absence thereof and are engineered to provide a known compression level to the system, consisting of the garment as well as the liner or padding that is used with the garment.

An example of the invention may include one or more of the following steps, functions, or structures:

obtaining a compression garment comprising (1) material having an end stretch, and (2) at least one gauge applied to the material;

applying the compression garment to a patient;

stretching, during the applying, the material until the at least one gauge indicates that a proper amount of stretch has been reached; and arriving, by the material during the stretching, at or near end stretch at substantially the same time that the at least one gauge indicates that the proper amount of stretch has been reached.

The example of the invention may also include one or more steps, functions, or structures set forth above combined with applying, by the compression garment after the applying, therapeutic compression to the patient.

The example of the invention may also include one or more steps, functions, or structures set forth above combined with the at least one gauge being tuned to the end stretch.

The example of the invention may also include one or more steps, functions, or structures set forth above combined with the material comprising short stretch material.

The example of the invention may also include one or more steps, functions, or structures set forth above combined with the end stretch corresponding to an elongation in the range of about 15% to about 100%.

The example of the invention may also include one or more steps, functions, or structures set forth above combined with the at least one gauge comprising a feature that forms a square to indicate that the proper amount of stretch has been reached.

The example of the invention may also include one or more steps, functions, or structures set forth above combined with the patient suffering from a sports injury and the therapeutic compression comprises 15-20 mmHg.

The example of the invention may also include one or more steps, functions, or structures set forth above combined with the patient being post operative and the therapeutic compression comprises 20-30 mmHg.

The example of the invention may also include one or more steps, functions, or structures set forth above combined with the patient suffering from Peripheral Arterial Disease (PAD) or mild lymphedema and the therapeutic compression comprises 20-30 mmHg.

The example of the invention may also include one or more steps, functions, or structures set forth above combined with the patient suffering from venous disease or significant lymphedema and the therapeutic compression comprises 30-40 mmHg.

The example of the invention may also include one or more steps, functions, or structures set forth above combined with the patient suffering from severe venous disease or severe lymphedema and the therapeutic compression comprises 40-50 mmHg.

Another example of the invention may include one or more of the following steps, functions, or structures:

a compression garment comprising an elastic material;

at least one gauge applied to the elastic material; and the at least one gauge tuned to indicate when a proper amount of stretch in the elastic material has been reached.

The example of the invention may also include one or more steps, functions, or structures set forth above combined with the proper amount of stretch being the end stretch of the elastic material.

The example of the invention may also include one or more steps, functions, or structures set forth above combined with the elastic material comprising short stretch material.

The example of the invention may also include one or more steps, functions, or structures set forth above combined with the end stretch corresponding to an elongation in the range of about 15% to about 100%.

The example of the invention may also include one or more steps, functions, or structures set forth above combined with the elastic material forming a plurality of bands wrappable about the limb of a patient.

The example of the invention may also include one or more steps, functions, or structures set forth above combined with the elastic material forming a sheet wrappable about the limb of a patient.

The example of the invention may also include one or more steps, functions, or structures set forth above combined with the sheet comprising a plurality of tabs formed along an edge thereof.

The example of the invention may also include one or more steps, functions, or structures set forth above combined with the at least one gauge comprising a feature.

The example of the invention may also include one or more steps, functions, or structures set forth above combined with the at least one gauge being tuned to the end stretch such that the feature forms a square at the same time the elastic material arrives at or near the end stretch.

The example of the invention may also include one or more steps, functions, or structures set forth above combined with the gauge comprising a plurality of tactile objects connected to and extending from the elastic material.

The example of the invention may also include one or more steps, functions, or structures set forth above combined with the gauge comprising a limiter.

The example of the invention may also include one or more steps, functions, or structures set forth above combined with the gauge comprising a limiter having slack therein when the elastic material is in a neutral or unstretched condition.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A system comprising:
   (a) a compression garment comprised at least in part of an elastic material forming a plurality of bands wrappable around a limb of a patient; and
   (b) at least one electronic gauge applied to the compression garment and adapted to indicate a predetermined amount of stretch that has been applied to the elastic material in position on the limb of the patient and/or adapted to indicate a predetermined level of compression being applied to the limb of the patient by the elastic material, wherein the electronic gauge includes an audible signal emitter that emits a sound indicative of whether the compression garment is being applied with proper, too little or too much compression.

2. A system according to claim 1, wherein the signal emitter emits a beep, series of beeps, or a tone at a specified frequency.

3. A system comprising:
   (a) a compression garment comprised at least in part of an elastic material forming a sheet wrappable around a limb of a patient; and
   (b) at least one electronic gauge applied to the compression garment and adapted a predetermined amount of stretch that has been applied to the elastic material in position on the limb of the patient and/or adapted to indicate a predetermined level of compression being applied to the limb of the patient by the elastic material, wherein the electronic gauge includes an audible signal emitter that emits a sound indicative of whether the compression garment is being applied with proper, too little or too much compression.

4. A system comprising:
   (a) a compression garment comprised at least in part of an elastic material forming a plurality of bands wrappable around a limb of a patient; and
   (b) at least one electronic gauge applied to the compression garment and adapted to indicate a predetermined amount of stretch that has been applied to the elastic material in position on the limb of the patient and/or adapted to indicate a predetermined level of compression being applied to the limb of the patient by the elastic material, wherein the electronic gauge is detachably secured to the compression garment by a thin film magnet.

5. A system comprising:
   (a) a compression garment comprised at least in part of an elastic material forming a sheet wrappable around a limb of a patient; and
   (b) at least one electronic gauge applied to the compression garment and adapted a predetermined amount of stretch that has been applied to the elastic material in position on the limb of the patient and/or adapted to indicate a predetermined level of compression being applied to the limb of the patient by the elastic material, wherein the electronic gauge is detachably secured to the compression garment by a thin film magnet.

6. A system comprising:
   (a) a compression garment comprised at least in part of an elastic material forming a plurality of bands wrappable around a limb of a patient;

(b) at least one electronic gauge applied to the compression garment and adapted to indicate a predetermined amount of stretch that has been applied to the elastic material in position on the limb of the patient and/or adapted to indicate a predetermined level of compression being applied to the limb of the patient by the elastic material;

(c) first and second fiducial markers positioned in spaced-apart relation on the garment, each fiducial marker being electrically conductive and including a piece of a magnetic or magnetically-attractable material; and (d) a linear potentiometer operationally associated with a strain gauge adapted to detect a change in resistance, inductance and/or capacitance between the first and second fiducial markers as the fiducial markers move relative to each other incident to the stretch of the elastic material.

7. A system according to claim 6, wherein the electronic gauge is adapted to measure and disclose a level of compression being applied to the limb of the patient by the elastic material.

8. A system according to claim 6, wherein the electronic gauge includes a visual indicator indicative of the compression being applied to the limb of the patient by the elastic material.

9. A system according to claim 8, wherein the visual indicator displays a color change indicative of the compression being applied to the limb of the patient by the elastic material.

10. A system according to claim 8, wherein the visual indicator displays a digital readout indicative of the compression being applied to the limb of the patient by the elastic material.

11. A system according to claim 8, wherein the visual indicator displays a digital readout indicative of the compression being applied to the limb of the patient by the elastic material by an application resident on a smart watch or smart phone adapted for digital communication with the electronic gauge.

12. A system according to claim 8, wherein the visual indicator comprises an array of LED light bars that provides a display indicative of the compression being applied to the limb of the patient by the elastic material.

13. A system according to claim 6, and including a plurality of electronic gauges positioned at predetermined locations on the compression garment to indicate the amount of stretch that has been applied to the elastic material at the predetermined locations on the compression garment.

14. A system according to claim 6, wherein the plurality of bands are adapted to extend concentrically around the limb of the patient.

15. A system according to claim 6, wherein each band of the plurality of bands includes an electronic gauge adapted to measure a value indicative of a level of compression of the elastic material of the band with which it is associated.

16. A system according to claim 6, wherein each electronic gauge is detachable from the compression garment and is adapted for reuse.

17. A system according to claim 6, wherein each electronic gauge is adapted to be detachably secured to the compression garment.

18. A system according to claim 6, wherein the elastic material comprises a short stretch elastic material.

19. A system according to claim 18, wherein the elastic material has an end stretch corresponding to an elongation in the range of approximately 15 percent to approximately 100 percent.

20. A system comprising:

(a) a compression garment comprised at least in part of an elastic material forming a sheet wrappable around a limb of a patient;

(b) at least one electronic gauge applied to the compression garment and adapted a predetermined amount of stretch that has been applied to the elastic material in position on the limb of the patient and/or adapted to indicate a predetermined level of compression being applied to the limb of the patient by the elastic material;

(c) first and second fiducial markers positioned in spaced-apart relation on the garment, each fiducial marker being electrically conductive and including a piece of a magnetic or magnetically-attractable material; and (d) a linear potentiometer operationally associated with a strain gauge adapted to detect a change in resistance, inductance and/or capacitance between the first and second fiducial markers as the fiducial markers move relative to each other incident to the stretch of the elastic material.

21. The system of claim 20, wherein the sheet includes a plurality of tabs formed along an edge of the sheet.

* * * * *